United States Patent [19]
Meyer et al.

[11] Patent Number: 5,069,708
[45] Date of Patent: Dec. 3, 1991

[54] PYRIMIDO(5,4-E)-AS-TRIAZINE-5,7(6H,8H)-DIONES

[75] Inventors: Norbert Meyer, Ladenburg; Ulrich Shirmer, Heidelberg; Peter Plath, Frankenthal; Bruno Wuerzer, Otterstadt; Karl-Otto Westphalen, Speyer, all of Fed. Rep. of Germany

[73] Assignee: BASF Aktiengesellschaft, Ludwigshafen, Fed. Rep. of Germany

[21] Appl. No.: 547,160

[22] Filed: Jul. 3, 1990

[30] Foreign Application Priority Data

Jul. 27, 1989 [DE] Fed. Rep. of Germany ....... 3923226
Jul. 27, 1989 [DE] Fed. Rep. of Germany ....... 3924845

[51] Int. Cl.$^5$ .................. C07D 487/04; A01N 43/90
[52] U.S. Cl. ........................................ 71/90; 71/93; 544/184
[58] Field of Search ....................... 544/184; 71/93, 90

[56] References Cited

U.S. PATENT DOCUMENTS 4,494,981 1/1985 Andrea et al. .......................... 71/93

FOREIGN PATENT DOCUMENTS 2901537 7/1980 Fed. Rep. of Germany .

OTHER PUBLICATIONS

Heterocycles, vol. 6, No. 11 (1977), pp. 1921-1923, Ichiba et al.,
Nishigaki et al., J. Heterocycl. Chem., vol. 19 1982, pp. 1309-1312.
Abstract Japanese Patent, 73/25,. 200 (1973).
Pfleiderer et al., Tetrahedron Letters, 1969, pp. 4699-4702.
Taylor et al., J. Org. Chem., vol. 40, No. 16, 1975, pp. 2321-2329.
Ichiba et al., J. Org. Chem., vol. 43, No. 3, 1978, pp. 469-472.
Chem. Ber. 105 (1972), 3334-335, Blankenhorn et al.
Chem. Pharm. Bull. 21 (2), (1973), pp. 448-450, Yoneda et al.
J. Heterocycl. Chem. 7 (6), (1970), p. 1443, Yoneda et al.
J. Med. Chem. 11 (5), (1968), pp. 1107-1108, Zee-Cheng et al.
Heterocycles, vol. 15, No. 1 (1981) Hirota et al.
J. Am. Chem. Soc. 90 (5), 1968, pp. 1374-1375.
J. Am. Chem. Soc. 31 (8), 1969, pp. 2143-2144.
Ullmanns Encyklopadie Der Technischen Chemie, vol. 12, 612-613 (1976).

Primary Examiner—John M. Ford
Attorney, Agent, or Firm—Keil & Weinkauf

[57] ABSTRACT

Herbicidal agents containing a pyrimido[5,4-e]-as-triazine-5,7-(6H,8H)-dione Ia

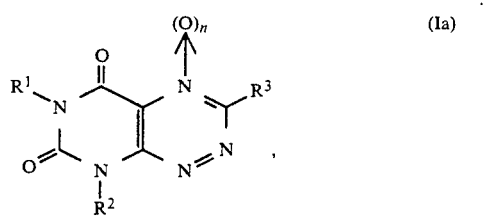

($R^1$, $R^2$=H, $C_1$-$C_6$-alkyl, $C_3$-$C_6$-cycloalkyl, $C_2$-$C_8$-alkenyl, phenyl or benzyl, $R^3$=H, halogen, nitro, $C_1$-$C_8$-alkyl which may carry up to three further substituents, $C_2$-$C_6$-alkenyl, phenyl-$C_2$-$C_6$-alkenyl, $C_3$-$C_6$-cycloalkyl which may carry up to 3 $C_1$-$C_4$-alkyl substituents, a 5- or 6-membered heterocyclic structure where up to 2 of the ring members are O, S or $NR^4$; —CO—$R^4$ or —CO—O—$R^4$; phenyl or hetaryl, which may carry up to 3 further substituents; or $ZR^6$; $R^4$=H, $C_1$-$C_6$-alkyl; Z=O, S or —N($R^7$)—; $R^6$=H, $C_1$-$C_6$-alkyl, phenyl or benzyl, which may carry up to 3 further substituents; $R^7$=H, $C_1$-$C_6$-alkyl or $R^6$ and $R^7$ together with nitrogen form a 5- or 6-membered ring which may contain O; n=0 or 1) or a salt of Ia with a mineral acid.

4 Claims, No Drawings

PYRIMIDO(5,4-E)-AS-TRIAZINE-5,7(6H,8H)-DIONES

The present invention relates to herbicides containing, as an active ingredient, a pyrimido[5,4-e]-as-triazine-5,7(6H,8H)-dione of the formula Ia

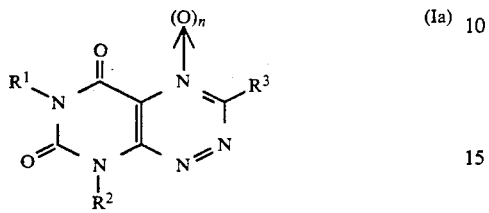

where $R^1$ and $R^2$ are each hydrogen, $C_1$–$C_6$-alkyl, $C_3$–$C_6$-cycloalkyl, $C_2$–$C_8$-alkenyl, phenyl or benzyl;

$R^3$ is hydrogen, halogen, nitro, $C_1$–$C_8$-alkyl which may carry up to three of the following substituents: halogen, hydroxyl, $C_1$–$C_6$-alkoxy, $C_1$–$C_6$-alkyl, $C_1$–$C_4$-alkoxy-$C_1$–$C_4$-alkoxy, $C_2$–$C_6$-alkenyl, $C_1$–$C_6$-alkylthio, phenyl or benzyl;

$C_2$–$C_6$-alkenyl or phenylalkenyl;

$C_3$–$C_6$-cycloalkyl which may carry up to three $C_1$–$C_4$-alkyl groups as substituents;

a 5-membered or 6-membered C-organic heterocyclic structure in which not more than two of the ring members, which should not be adjacent to one another, may be —O—, —S— or —N($R^4$)—, where $R^4$ is hydrogen or $C_1$–$C_6$-alkyl; —CO—$R^4$ or —CO—O—$R^4$;

phenyl or a mononuclear hetaryl radical, where these groups may contain up to three of the following substituents: halogen, nitro, $C_1$–$C_6$-alkyl, $C_2$–$C_6$-alkenyl, $C_1$–$C_6$-alkoxy or an amino group —$NR^4R^5$, where $R^5$ is one of the radicals $R^4$;

—$ZR^6$, where Z is oxygen, sulfur or a group —N($R^7$)— and $R^6$ is hydrogen, $C_1$–$C_6$-alkyl or a phenyl or benzyl group which may carry up to three of the following substituents on the nucleus: $C_1$–$C_6$-alkyl, $C_1$–$C_6$-alkoxy or halogen, and where $R^7$ is hydrogen or $C_1$–$C_6$-alkyl, and $R^6$ and $R^7$ together with the nitrogen atom may furthermore form a 5-membered or 6-membered ring which may be interrupted by oxygen, and n is 0 or 1, or a salt of Ia with a mineral acid which does not adversely affect the herbicidal action of Ia.

The present invention furthermore relates to novel pyrimido[5,4-e]-as-triazine-5,7(6H,8H)-dione derivatives of the formula Ib

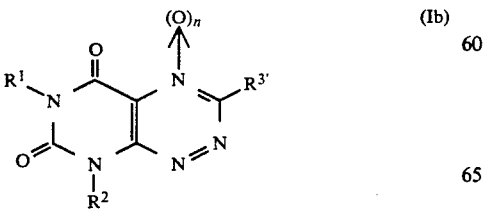

where $R^{3'}$ is $C_1$–$C_8$-alkyl having one or two of the following substituents: halogen, hydroxyl, $C_1$–$C_6$-alkoxy, $C_1$–$C_4$-alkoxy-$C_1$–$C_4$-alkoxy or $C_1$–$C_6$-alkylthio;

$C_3$–$C_6$-cycloalkyl which may carry up to three $C_1$–$C_4$-alkyl groups as substituents;

a 5-membered or 6-membered saturated heterocyclic structure having the group —N($R^4$)— as a hetero group, where $R^4$ is $C_1$–$C_6$-alkyl, or having two non-adjacent hetero atoms, which may be oxygen, sulfur or a group —N($R^4$)—;

—CO—$R^4$ or —CO—O—$R^4$;

a mononuclear hetaryl radical which contains from one to three of the following substituents: halogen, nitro, $C_1$–$C_6$-alkyl, $C_2$–$C_6$-alkenyl, $C_1$–$C_6$-alkoxy or an amino group —$NR^4$—$R^5$, where $R^5$ is one of the radicals $R^4$;

$C_2$–$C_6$-alkoxy;

—$ZR^6$, where Z is oxygen, sulfur or a group —N($R^7$)— and $R^6$ is hydrogen, $C_2$–$C_6$-alkyl or a phenyl or benzyl group, each of which may carry up to three of the following substituents on the nucleus: $C_1$–$C_6$-alkyl, $C_1$–$C_6$-alkoxy or halogen, and where $R^7$ is $C_1$–$C_6$-alkyl, and $R^6$ and $R^7$ together with the nitrogen atom may furthermore form a 5-membered or 6-membered ring which may also be interrupted by oxygen, and the salts of Ib with acids which do not adversely affect the herbicidal action of Ib.

The papers by K. Senga et al. (Heterocyclus 6 (1977), 1921 et seq. and J. Heterocycl. Chem. 19 (1982), 1309 et seq.) disclose compounds of type Ia which carry methyl in the 6- and 8-positions and are unsubstituted or carry an anilino group or a substituted phenyl group in the 3-position.

JA-A 73 25 200 discloses compounds of type Ia which carry hydrogen, a hydrocarbon radical or an amine radical in the 8-position and are unsubstituted or carry a hydrocarbon group or an aromatic radical in the 3-position.

These compounds and their addition salts with acids are attributed antimicrobial, fungicidal and anti-viral properties in the stated literature. However, these compounds are not known to have a herbicidal action.

It is an object of the present invention to provide novel herbicides having a stronger herbicidal effect, since the action of the known herbicides is not always satisfactory. It is a further object of the present invention to provide novel herbicidal compounds.

We have found that these objects are achieved by the herbicides defined at the outset and containing the compounds Ia as active ingredient, and the novel compounds Ib which are covered by the general formula Ia.

Preferred compounds Ia in the novel agents are those in which the substituents have the following meanings:

$R^1$ and $R^2$ are each hydrogen, straight-chain or branched $C_1$–$C_6$-alkyl, in particular $C_1$–$C_4$-alkyl, such as methyl, ethyl, n-propyl, isopropyl or butyl, $C_3$–$C_6$-cycloalkyl, in particular cyclopropyl or cyclohexyl, $C_2$–$C_8$-alkenyl, in particular vinyl or allyl, phenyl or benzyl;

$R^3$ is hydrogen, halogen, in particular chlorine or bromine, or nitro; straight-chain or branched $C_1$–$C_8$-alkyl, in particular $C_1$–$C_4$-alkyl, which may carry up to three of the following substituents: halogen, such as fluorine, chlorine or bromine, hydroxyl, $C_1$–$C_6$-alkoxy, such as methoxy or ethoxy, $C_1$–$C_6$-alkyl, such as methyl, ethyl, n-propyl, isopropyl or tert-butyl, $C_1$–$C_4$-alkoxy-$C_1$–$C_4$- alkoxy, such as methoxymethoxy, 2-methoxyethoxy or tert-butoxymethoxy, $C_2$-$C_6$-alkenyl, such as ethenyl, 2-propenyl, 2-butenyl or 3-butenyl, $C_1$-$C_6$-alkylthio, such as methylthio, ethylthio or tert-butylthio, phenyl and/or benzyl; methyl, ethyl, n-propyl, isopropyl, 2-methylprop-1-yl, n-butyl, tert-butyl or 3,3-dimethylbut-1-yl, dibromomethyl, trichloromethyl, methoxymethyl, 1-methoxyeth-1-yl, 2-methoxyethyl, 1-hydroxyeth-1-yl, methylthioeth-2-yl, 1-methyl(2,5-dioxa)hexyl, 2-phenethyl or 1,2-dibromophenethyl are particularly preferred;

$C_2$-$C_6$-alkenyl or phenylalkenyl, in particular allyl, but-2-en-2-yl or styryl;

$C_3$-$C_6$-cycloalkyl which may carry up to three $C_1$-$C_4$-alkyl groups as substituents, in particular cyclopropyl, cyclopentyl or cyclohexyl, a 5-membered or 6-membered saturated heterocyclic structure, in particular 4-tetrahydropyranyl or 3-tetrahydrothiopyranyl;

acetyl, such as methoxycarbonyl, ethoxycarbonyl or butoxycarbonyl;

phenyl or a mononuclear hetaryl radical, where these groups may contain up to three of the following substituents: halogen, such as fluorine, chlorine or bromine, nitro, $C_1$-$C_6$-alkyl, such as methyl, ethyl or tert-butyl, $C_2$-$C_6$-alkenyl, such as ethenyl, 2-propenyl or 2-butenyl, $C_1$-$C_6$-alkoxy, such as methoxy, ethoxy or tert-butoxy, amino, $C_1$-$C_6$-alkylamino, such as methylamino or ethylamino, or di-$C_1$-$C_6$-alkylamino, such as dimethylamino; phenyl, 4-chlorophenyl, 4-nitrophenyl, 4-(dimethylamino)phenyl, 2-pyridyl, 3-pyridyl, 3-pyridyl.HCl, 4-pyridyl, 2-thienyl, 3-thienyl, 1-ethylpyrazol-4-yl, 3-methylisoxazol-5-yl, 2-(prop-3-yl)-isoxazol-5-yl, 3-propylisoxazol-5-yl or 3-butylisoxazol-5-yl;

a radical which is bridged via oxygen, sulfur or nitrogen, in particular methoxy, ethoxy, phenoxy, 4-chlorophenoxy, benzyloxy, 4-chlorobenzyloxy, methylthio, phenylthio, isopropylamino, N,N-diethylamino, anilino, 4-chloroanilino, N-methylanilino, pyrrolidino or N-morpholino.

Preferred novel pyrimido[5,4-e]-as-triazine-5,7(6H,8H)-diones of the formula Ib are listed in Table 1 under the Examples.

Suitable addition salts with acids are the salts of acids which do not adversely affect the herbicidal action of the compounds Ia, for example the hydrochlorides, hydrobromides, sulfates, nitrates, phosphates, oxalates or dodecylbenzenesulfonates.

The 3,6,8-substituted pyrimido[5,4-e]-as-triazine-5,7(6H,8H)-diones Ia are known or (in the case of Ib) are obtainable in a conventional manner. Where $R^3$ or $R^{3'}$ is not —$ZR^6$ or halogen and n is 0, the compounds can be prepared according to the following scheme.

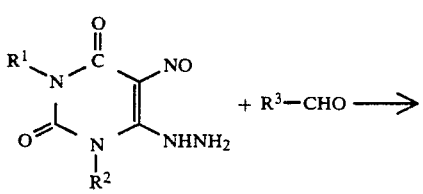

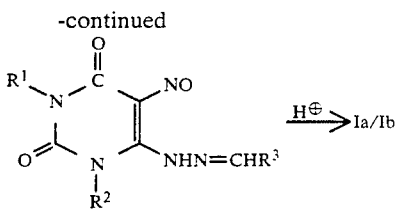

This reaction is disclosed in, for example, the papers by G. Blankenhorn and W. Pfleiderer (Chem. Ber. 105 (1972), 3334 et seq.) and K. Senga et al. (Heterocyclus, 6 (1977), 1921 et seq.). The hydrazones are synthesized in a known manner (cf. Houben-Weyl, Methoden der Organischen Chemie, Volume VII.1, page 461 et seq.).

The preparation of the hydrazones and their cyclization are preferably carried out in an alcohol, such as ethanol, using a catalytic amount of a mineral acid, such as hydrochloric acid or sulfuric acid, at the boiling point of the solvent. It is preferable to use stoichiometric amounts or a slight excess of the aldehyde. In general, the reaction is carried out under atmospheric pressure or under the autogenous pressure of the particular solvent, unless a higher pressure, for example up to 5 bar, is advisable owing to readily volatile reactants.

In the preparation of compounds of the formula Ia, the particular N-oxides (n=1) may be obtained as by-products. These can also be synthesized in a controlled manner by known processes (e.g. K. Senga et al., J. Org. Chem. 43 (1978), 469 et seq.).

The pyrimido[5,4-e]-as-triazine-5,7(6H,8H)-diones of the formula Ia (n=0) or Ib, with the exception of the compounds where $R^3$ and $R^{3'}$ are $ZR^6$ or halogen, can also be prepared by synthesizing the corresponding hydrazones IIb from 4-hydrazineuracils of the formula IIa by known processes (for example W. Pfleiderer and G. Blankenhorn, THL, 1969, page 4699 et seq.) and then carrying out nitrosation at from 20° C. to the boiling point of the solvent. Spontaneous cyclization takes place to give the compounds Ia (n=0) or Ib.

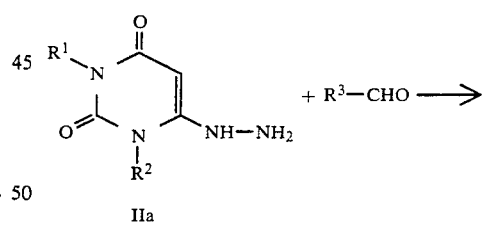

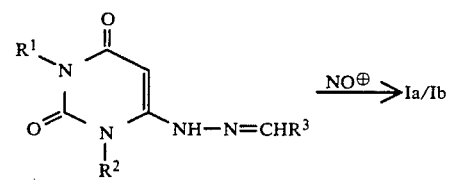

The hydrazine Va and the aldehyde are preferably reacted in stoichiometric amounts or using a slight excess of aldehyde.

The nitrosation is preferably carried out using an organic nitrite, such as amyl or isoamyl nitrite or using an inorganic nitrite, such as sodium nitrite or potassium nitrite.

Preferred solvents are polar solvents, such as lower alcohols or water, advantageously with a catalytic amount of an acid, such as hydrochloric acid or sulfuric acid.

This reaction too is preferably carried out under atmospheric pressure.

Compounds of the formula Ia and Ib where $R^1$ or $R^2$ is hydrogen and $R^3$ or $R^{3'}$ is not $ZR^6$ or halogen are also obtainable by debenzylation of the corresponding compounds Ia or Ib ($R^1$ or $R^2$=benzyl) with hydrogen in the presence of a hydrogenation catalyst, such as palladium/carbon.

Compounds of the formula Ia or Ib where $R^3$ or $R^{3'}$ is halogen can be obtained by reacting a pyrimido[5,4-e]-as-triazine-5,7(6H,8H)-dione with, for example, POCl$_3$ and diethylaniline as an auxiliary base (for example E. C. Taylor and F. Sowinski, JOC 40 (1975), 2321 et seq.).

The compounds Ia or Ib where $R^3$ and $R^{3'}$ are each —$ZR^6$ are synthesized by reacting the corresponding chlorine derivative ($R^3$ and $R^{3'}$=chlorine) with a nucleophile of the formula H—$ZR^6$ or H—N($R^6R^7$) in an inert solvent (for example K. Senga, J. Heterocycl. Chem. 19 (1982), 1309 et seq.).

Suitable solvents are ethers, such as dioxane or tetrahydrofuran, or advantageously the corresponding alcohol HO—$R^6$ in excess. If Z is sulfur or —$NR^7$, ethers or lower alcohols, such as methanol or isopropanol, esters, such as acetonitrile, or amides, such as dimethylformamide, can be used. The synthesis is preferably carried out in tetrahydrofuran.

The auxiliary base used is either a salt of the alcohol or of the thiol H—Z—$R^6$ or excess amine H—$NR^6R^7$ or a tertiary amine, such as triethylamine, N-methylpiperidine or N-methylmorpholine.

The compound H—$ZR^6$ and the auxiliary base are advantageously used in not less than equimolar amounts, preferably in about 10% excess, based on the chlorine derivative ($R^3$ or $R^{3'}$=Cl). The reaction is advantageously carried out at from 0° to 100° C., preferably from 40° to 80° C.

Regarding the pressure, the above statements for the preparation of the compound Ia or Ib where $R^3$ or $R^{3'}$ is not —$ZR^6$ or halogen and n is 0 are applicable.

The compounds Ia and Ib and their salts conforming to the definition are suitable as herbicides. Preparation Examples

EXAMPLE 1

3-(3-Tetrahydrothiopyranyl)-6,8-dimethyl-pyrimido[5,4-e]-as-triazine-5,7(6H,8H)-dione

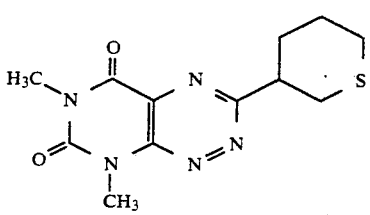

2.6 g (0.02 mol) of tetrahydrothiopyran-3-carbaldehyde and 2 drops of concentrated hydrochloric acid were added to 3 g (0.015 mol) of 5-nitroso-4-hydrazino-1,3-dimethyluracil in 100 ml of ethanol. Refluxing was carried out for 3 hours, after which the solvent was removed and the residue was taken up in ethyl acetate. This solution was filtered over silica gel and the filtrate was evaporated down again. The product thus obtained was then recrystallized from diethyl ether. Yield: 66%, mp.: 134°–138° C.

EXAMPLE 2

3-(4-Morpholino)-6,8-dimethylpyrimido[5,4-e]-as-triazine-5,7(6H,8H)-dione

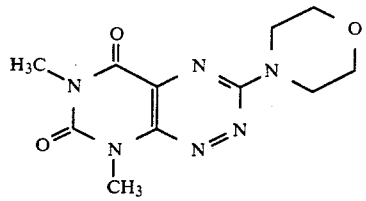

1.75 g (0.02 mol) of morpholine were added to a suspension of 2.3 g (0.01 mol) of 3-chloro-6,8-dimethyl-pyrimido[5,4-e]-as-triazine-5,7(6H,8H)-dione (3-chlorofervenuline) in 70 ml of tetrahydrofuran. The mixture was heated at 70° C. for 30 minutes and then evaporated down under reduced pressure, and the residue was stirred with water, filtered off and recrystallized from isopropanol. Yield: 70%, mp.: 180°–182° C.

The novel compounds listed in Table 1 were prepared similarly to Examples 1 and 2.

Table 2 lists the known compounds of type Ia, which, in addition to compounds Ib, are preferred as herbicidal active ingredients.

TABLE 1

Novel pyrimido[5,4-e]-as-triazin-5,7(6H,8H)-diones Ib

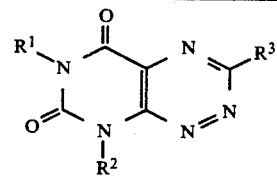

| Ex. | $R^1$ | $R^2$ | $R^3$ | mp./NMR data (δ[ppm], multiplicity, integral) |
|---|---|---|---|---|
| 1 | methyl | methyl | tetrahydrothiopyran-3-yl | 134–138° C. |
| 2 | " | " | N-morpholinyl | 180–182° C. |
| 3 | " | " | dibromomethyl | 198–200° C. (decomp.) |
| 4 | " | " | acetyl | 152–153° C. (decomp.) |

TABLE 1-continued

Novel pyrimido[5,4-e]-as-triazin-5,7(6H,8H)-diones Ib

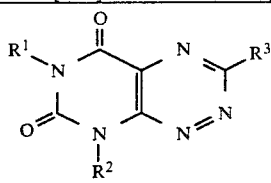

| Ex. | R¹ | R² | R³ | mp./NMR data (δ[ppm], multiplicity, integral) |
|---|---|---|---|---|
| 5 | " | " | 1-(1-hydroxy)ethyl | 154–157° C. |
| 6 | " | " | 1,2-dibromophenethyl | 201° C. |
| 7 | " | " | 4-tetrahydropyranyl | 155–158° C. |
| 8 | " | " | cyclohexyl | 183–187° C. |
| 9 | " | " | cyclopentyl | 156–157° C. |
| 10 | " | " | 2-(2-butenyl) | 181–184° C. |
| 11 | " | " | 1-(1-methoxyethyl) | 125–128° C. |
| 12 | " | " | methoxymethyl | 3.5(s, 3H);3.55(s, 3H); 3.9(s, 3H);5.0(s, 2H) |
| 13 | " | " | methoxyethyl | 3.4(s, 3H);3.6(s, 3H); 3.9(s, 3H);4.05(t, 2H); |
| 14 | " | " | methylthioethyl | 86–90° C. |
| 15 | " | " | 1-methyl-(2,5-dioxa)hexyl | 59–62° C. |
| 16 | " | " | 5-(3-butyl)isoxazolyl | 123–126° C. |
| 17 | " | " | 4-(1-ethyl)pyrazolyl | 215–217° C. |
| 18 | " | " | 5-(3-propyl)isoxazolyl | 159–161° C. |
| 19 | " | " | 5-(3-2-propyl)isoxazolyl | 123–126° C. |
| 20 | " | " | 5-(3-methyl)isoxazolyl | >200° C. (decomp.) |
| 21 | " | allyl | 3-tetrahydrothiopyranyl | 105–109° C. |
| 22 | " | propyl | 3-tetrahydrothiopyranyl | 101–103° C. |
| 23 | methyl | allyl | 4-tetrahydropyranyl | 3.4–3.7(m, 1H, 2H, with s, 3H);4.1–4.2(m, 2H); 5.1(d, 2H) |
| 24 | " | propyl | 4-tetrahydropyranyl | 90–93° C. |
| 25 | " | allyl | cyclohexyl | 68–71° C. |
| 26 | " | propyl | " | 1.0(t, 3H); 1.1–2.1(m, 10H); |
| 27 | " | allyl | methylthioethyl | 2.2(s, 3H);3.1(t, 3H); 3.6(s, 3H);5.1(d, 2H) |
| 28 | " | propyl | methylthioethyl | 1.0(t, 3H);2.2(s, 3H); 3.1(t, 2H);3.6(s, 3H); 4.5(t, 2H) |
| 29 | " | methyl | methoxycarbonyl | 151–155° C. |
| 30 | " | " | ethoxycarbonyl | 1.5(t, 3H);3.6(s, 3H); 4.0(s, 3H);4.6(q, 2H) |
| 31 | " | " | butoxycarbonyl | 1.0(t, 3H);1.4–1.6 |
| 32 | propyl | propyl | cyclohexyl | 3.3(m, 1H);4.1(t, 2H); 4.5(t, 2H) |
| 33 | 2-propyl | 2-propyl | " | 3.3(m, 1H);5.3(m, 1H); 5.8(m, 1H) |
| 34 | ethyl | ethyl | " | 3.3(m, 1H);4.2(m, 2H); 4.6(m, 2H) |
| 35 | methyl | methyl | cyclopropyl | 131–133° C. |
| 36 | " | propyl | " | 54–57° C. |
| 37 | " | allyl | " | 1.2–1.4(m, 4H);2.6(m, 1H); 3.5(s, 3H);5.1(d, 2H) |
| 38 | ethyl | ethyl | " | 137–139 |
| 39 | methyl | methyl | pyrrolidino | |

TABLE 2

Herbicidal pyrimido[5,4-e]-as-triazin-5,7(6H,8H)-diones Ia

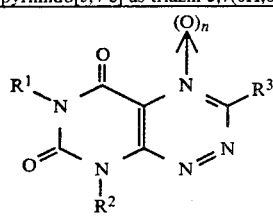

| Ex. | R¹ | R² | R³ | n | mp./NMR data (δ[ppm], multiplicity, integral) |
|---|---|---|---|---|---|
| 40 | methyl | methyl | methyl | 0 | 181–182° C. |
| 41 | " | " | H | 0 | 178–179° C. |
| 42 | " | " | phenyl | 0 | 270° C. |
| 43 | " | " | 4-chlorophenyl | 0 | 275° C. |

TABLE 2-continued

Herbicidal pyrimido[5,4-e]-as-triazin-5,7(6H,8H)-diones Ia

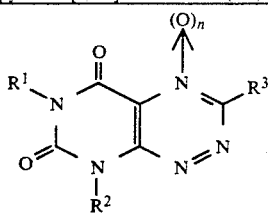

| Ex. | R¹ | R² | R³ | n | mp./NMR data (δ[ppm], multiplicity, integral) |
|---|---|---|---|---|---|
| 44 | " | " | 4-nitrophenyl | 0 | 323° C. |
| 45 | " | " | 2-propyl | 0 | 158–159° C. |
| 46 | " | " | 4-(dimethylamino)phenyl | 0 | 340° C. (decomp.) |
| 47 | " | " | trichloromethyl | 0 | 194° C. |
| 48 | " | " | ethyl | 0 | 95° C. |
| 49 | " | " | tert.-butyl | 0 | 198–199° C. |
| 50 | " | " | chloro | 0 | 147° C. |
| 51 | " | " | H | 1 | 179–180° C. |
| 52 | methyl | ethyl | methyl | 0 | 132–133° C. |
| 53 | methyl | ethyl | 2-propyl | 0 | 107–109° C. |
| 54 | ethyl | methyl | methyl | 0 | 115–117° C. |
| 55 | ethyl | methyl | 2-propyl | 0 | 76–78° C. |
| 56 | benzyl | methyl | methyl | 0 | >177° C. (decomp.) |
| 57 | benzyl | methyl | 2-propyl | 0 | 135–137° C. |
| 58 | methyl | benzyl | methyl | 0 | 213–217° C. |
| 59 | methyl | benzyl | 2-propyl | 0 | 198–200° C. |
| 60 | allyl | methyl | methyl | 0 | 3.0(s, 3H);3.9(s, 3H); 4.7(d, 2H) |
| 61 | allyl | methyl | 2-propyl | 0 | 1.5(d, 6H);3.6(q, 1H); 3.9(s, 3H);4.7(d, 2H) |
| 62 | methyl | allyl | methyl | 0 | 125–127° C. |
| 63 | methyl | allyl | 2-propyl | 0 | 93–95° C. |
| 64 | methyl | propyl | 2-propyl | 0 | 52–53° C. |
| 65 | methyl | propyl | methyl | 0 | 104–106° C. |
| 66 | methyl | 2-propyl | methyl | 0 | 112–114° C. |
| 67 | 2-propyl | methyl | methyl | 0 | 135–137° C. |
| 68 | methyl | methyl | benzyl | 0 | 180–182° C. |
| 69 | methyl | methyl | styryl | 0 | 263° C. |
| 70 | methyl | methyl | 1-(3,3-dimethyl)butyl | 0 | 134–136° C. |
| 71 | methyl | methyl | 1-(2-methyl)propyl | 0 | 86–90° C. |
| 72 | cyclohexyl | methyl | methyl | 0 | 135–138° C. |
| 73 | " | methyl | 2-propyl | 0 | 103–106° C. |
| 74 | methyl | H | methyl | 0 | 168–174° C. |
| 75 | methyl | methyl | 2-pyridyl | 0 | 266–269° C. |
| 76 | methyl | methyl | 3-pyridyl | 0 | 121–125° C. |
| 77 | methyl | methyl | 4-pyridyl | 0 | 269–271° C. |
| 78 | methyl | methyl | 2-thienyl | 0 | 285–288° C. |
| 79 | methyl | methyl | 3-thienyl | 0 | 311–325° C. |
| 80 | methyl | H | 2-propyl | 0 | 185–188° C. |
| 81 | methyl | methyl | 2-propyl | 1 | 172–174° C. |
| 82 | methyl | allyl | ethyl | 0 | 70–73° C. |
| 83 | methyl | propyl | ethyl | 0 | 79–82° C. |
| 84 | methyl | allyl | 1-(2-methyl)propyl | 0 | 76–79° C. |
| 85 | methyl | propyl | 1-(2-methyl)propyl | 0 | 35° C. |
| 86 | methyl | allyl | 3-pyridyl | 0 | 154–156° C. |
| 87 | methyl | propyl | 3-pyridyl | 0 | 159–162° C. |
| 88 | propyl | propyl | H | 0 | 77–80° C. |
| 89 | propyl | propyl | methyl | 0 | 3.0(s, 3H);4.1(t, 2H); 4.5(t, 2H) |
| 90 | propyl | propyl | 2-propyl | 0 | 3.6(m, 1H);4.1(t, 2H); 4.5(t, 2H) |
| 91 | propyl | propyl | 3-pyridyl.HCl | 0 | 199–203° C. |
| 92 | 2-propyl | 2-propyl | H | 0 | 5.3(m, 1H);5.9(m, 1H); 9.9(2, 1H) |
| 93 | " | " | methyl | 0 | 3.0(s, 3H);5.3(m, 1H); 5.8(m, 1H) |
| 94 | " | " | 2-propyl | 0 | 3.6(m, 1H);5.3(m, 1H); 5.8(m, 1H) |
| 95 | " | " | 3-pyridyl | 0 | 191–194° C. |
| 96 | ethyl | ethyl | methyl | 0 | 100–103° C. |
| 97 | ethyl | ethyl | 2-propyl | 0 | 107–109° C. |
| 98 | ethyl | ethyl | 3-pyridyl.HCl | 0 | 239–240° C. |
| 99 | ethyl | ethyl | H | 0 | 168–170° C. |
| 100 | methyl | methyl | methoxy | 0 | 144–145° C. |
| 101 | methyl | methyl | benzyloxy | 0 | 185–187° C. |
| 102 | methyl | methyl | phenoxy | 0 | |
| 103 | methyl | methyl | 4-Cl-phenoxy | 0 | |
| 104 | methyl | methyl | 4-Cl-benzyloxy | 0 | 190–192° C. |
| 105 | methyl | methyl | methylthio | 0 | 157–160° C. |

TABLE 2-continued
Herbicidal pyrimido[5,4-e]-as-triazin-5,7(6H,8H)-diones Ia

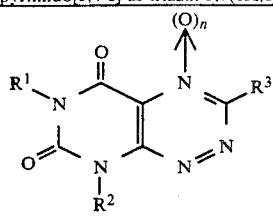

| Ex. | R$^1$ | R$^2$ | R$^3$ | n | mp./NMR data (δ[ppm], multiplicity, integral) |
|-----|-------|-------|-------|---|----------------------------------------------|
| 106 | methyl | methyl | anilino | 0 | 245–248° C. |
| 107 | methyl | methyl | 4-chloroanilino | 0 | 248–250° C. |
| 108 | methyl | methyl | N-methylanilino | 0 | |
| 109 | methyl | methyl | isopropylamino | 0 | |
| 110 | methyl | methyl | N,N-diethylamino | 0 | |
| 111 | ethyl | ethyl | H | 1 | 165–168° C. |

The pyrimido[5,4-e]-as-triazin-5,7(6H, 8)-diones Ia, or the herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

The compounds Ia and Ib are suitable for the preparation of solutions, emulsions, pastes and oil dispersions to be sprayed direct. Examples of inert additives are mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient. The active ingredients are employed in a purity of from 90 to 100, and preferably from 95 to 100, % (according to the NMR spectrum).

Compounds Ia and Ib may be formulated for instance as follows:

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 28 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 3 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 4 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 5 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 86 is intimately mixed with 97 parts by weight of particulate kaolin. A dust is obtained containing 3% by weight of the active ingredient.

VII. 30 parts by weight of compound no. 7 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 86 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 5.0, preferably 0.01 to 2.0, kg of active ingredient per hectare.

In view of the numerous application methods possible, the compounds according to the invention, or agents containing them, may be used in a large number of crops. Those which follow are given by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |

-continued

| Botanical name | Common name |
| --- | --- |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Triticum durum | durum wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |

| Botanical name | Common name |
| --- | --- |
| Zea mays | Indian corn, sweet corn, maize |

To increase the spectrum of action and to achieve synergistic effects, the pyrimido[5,4-e]-as-triazine-5,7-(6H, 8H)-diones Ia and Ib may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, quinolinecarboxylic acids, (hetero)-aryloxyphenoxypropionic acid derivatives (salts, esters, amides), etc.

It may also be useful to apply the compounds Ia and Ib, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

USE EXAMPLES

The herbicidal action of the pyrimido[5,4-e]-as-triazine-5,7-(6H, 8H)-diones of the formula Ia and Ib on the growth of the test plants is illustrated in the following greenhouse experiments.

The vessels employed were plastic flowerpots having a volume of 300 cm$^3$ and filled with a sandy loam containing about 3.0% humus. The seeds of the test plants were sown separately, according to species.

In the preemergence treatment, the active ingredients, suspended or emulsified in water, were applied through finely distributing nozzles immediately after sowing. The vessels were lightly irrigated to induce germination and growth, and covered with transparent plastic hoods until the plants had taken root. This cover ensured uniform germination of the test plants, insofar as this was not impaired by the active ingredients.

For the postemergence treatment, the plants were grown, depending on growth form, to a height of 3 to 15 cm before being treated with the active ingredients, which were suspended or emulsified in water. The application rate for postemergence treatment was 0.5 kg/ha.

The pots were set up in the greenhouse, species from warmer climates in warmer areas (20° to 35° C.) and species from moderate climates at 10° to 25° C. The experiments were run for from 2 to 4 weeks. During this time the plants were tended and their reactions to the various treatments assessed.

The assessment scale was 0 to 100, 100 denoting nonemergence or complete destruction of at least the visible plant parts, and 0 denoting no damage or normal growth.

The plants used in the experiments were Amaranthus retroflexus, Chrysanthemum coronarium, Setaria italica and Triticum aestivum.

Compounds 28, 82 and 86, applied postemergence, provided excellent control of unwanted broadleaved plants, and were very well tolerated by the crop plant wheat.

We claim:

1. A process for combating the growth of unwanted plants, wherein a herbicidally effective amount of a compound of the formula Ia

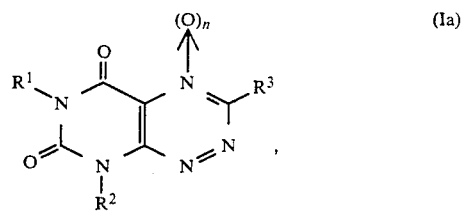

where

R$^1$ and R$^2$ are each hydrogen, C$_1$-C$_6$-alkyl, C$_3$-C$_6$-cycloalkyl, C$_2$-C$_8$-alkenyl, phenyl or benzyl;

R$^3$ is hydrogen, halogen, nitro, C$_1$-C$_8$-alkyl which may carry up to three of the following substituents: halogen, hydroxyl, C$_1$-C$_6$-alkoxy, C$_1$-C$_6$-alkyl, C$_1$-C$_4$-alkoxy-C$_1$-C$_4$-alkoxy, C$_2$-C$_6$-alkenyl, C$_1$-C$_6$-alkylthio, phenyl or benzyl;

C$_2$-C$_6$-alkenyl or phenylalkenyl;

C$_3$-C$_6$-cycloalkyl which may carry up to three C$_1$-C$_4$-alkyl groups as substituents;

4-tetrahydropyranyl or 3-tetrahydrothiopyranyl;

—CO—R$^4$ or —CO—O—R$^4$;

where R$^4$ is hydrogen or C$_1$-C$_6$-alkyl;

4-chlorophenyl, phenyl, 4-nitrophenyl, 4-(dimethylamino)-phenyl, 2-pyridyl, 3-pyridyl, 3-pyridyl.HCl, 4-pyridyl, 2-thienyl, 3-thienyl, 1-ethylpyrazol-4-yl, 3-methylisoxazol-5-yl, 2-(prop-3-yl)-isoxazol-5-yl, 3-propylisoxazol 5-yl or 3-butylisoxazol-5-yl; phenyl substituted by one to three of the following substituents: halogen, nitro, C$_1$-C$_6$-alkyl, C$_2$-C$_6$-alkenyl, C$_1$-C$_6$-alkoxy or an amino group -NR$^4$R$^5$, where R$^5$ is one of the radicals R$^4$; ZR$^6$, where Z is oxygen, sulfur or a group —(NR$^7$)— and R$^6$ is hydrogen, C$_1$-C$_6$-alkyl or a phenyl or benzyl group which may carry up to three of the following substituents on the nucleus: C$_1$-C$_6$-alkyl, C$_1$-C$_6$-alkoxy or halogen, and where R$^7$ is hydrogen or C$_1$-C$_6$-alkyl, pyrrolidino and N-morpholino; and n is 0 or 1, or a salt of Ia with a mineral acid is allowed to act on plants, their habitat or on seed.

2. A process as defined in claim 1, wherein in the compound Ia R$^1$ is methyl R$^2$ is propyl and R$^3$ is methylthioethyl.

3. A process as defined in claim 1, wherein in the compound Ia R$^1$ is methyl, R$^2$ is allyl and R$^3$ is ethyl.

4. A process as defined in claim 1, wherein R$^1$ is methyl, R$^2$ is allyl and R$^3$ is 3-pyridyl.

* * * * *

UNITED STATES PATENT AND TRADEMARK OFFICE
CERTIFICATE OF CORRECTION

PATENT NO. : 5,069,708

DATED : December 3, 1991

INVENTOR(S) : Norbert MEYER et al.

It is certified that error appears in the above-identified patent and that said Letters Patent is hereby corrected as shown below:

On the Cover Page

The inventor whose name reads "Shirmer" should read --Schirmer--

In the Foreign Application Priority Data, the date of the first listed reference reading "Jul. 27, 1989" should read --Jul. 14, 1989--

In the Abstract, Line 4, that part reading "benzyl, $R^3$=H," should read --benzyl; $R^3$=H,--

Signed and Sealed this

Thirteenth Day of April, 1993

Attest:

STEPHEN G. KUNIN

*Attesting Officer*  *Acting Commissioner of Patents and Trademarks*